(12) United States Patent
Ciaff

(10) Patent No.: US 6,871,100 B2
(45) Date of Patent: Mar. 22, 2005

(54) APPARATUS FOR THE DIAGNOSIS AND THERAPY OF NEURO-MUSCULAR AND OTHER TISSUE DISORDERS

(75) Inventor: Roberto Ciaff, Fetcham (GB)

(73) Assignee: Q Science LTD, London (GB)

( * ) Notice: Subject to any disclaimer, the term of this patent is extended or adjusted under 35 U.S.C. 154(b) by 397 days.

(21) Appl. No.: 09/825,618

(22) Filed: Apr. 3, 2001

(65) Prior Publication Data

US 2003/0100932 A1 May 29, 2003

(30) Foreign Application Priority Data

Dec. 23, 2000 (GB) .............................................. 0031654

(51) Int. Cl.⁷ ................................................. A61N 1/08
(52) U.S. Cl. ............................. 607/48; 607/46; 607/50; 607/115
(58) Field of Search ................................. 607/115, 145, 607/150, 46, 48, 50

(56) References Cited

U.S. PATENT DOCUMENTS 1,557,417 A * 10/1925 Cheney ........................ 601/20
4,620,543 A    11/1986 Heppenstall et al. ...... 128/419 F
4,830,009 A     5/1989 Schmitt et al. ............. 128/421
4,846,181 A *   7/1989 Miller .......................... 607/50
4,976,263 A    12/1990 Seidl et al. ................. 128/421
5,562,718 A * 10/1996 Palermo ...................... 607/46

FOREIGN PATENT DOCUMENTS

| DE | 3546419 A1 | 7/1987 |
| EP | 203336 A1 | 12/1986 |
| GB | 2156682 A | 10/1985 |
| GB | 2175504 A | 12/1986 |
| GB | 2175806 A | 12/1986 |

* cited by examiner

Primary Examiner—Angela D. Sykes
Assistant Examiner—Roderick Bradford
(74) Attorney, Agent, or Firm—Lahive & Cockfield, LLP

(57) ABSTRACT

An apparatus for the diagnosis and/or therapy of neuro-muscular disorders, comprising;

a control module for controlling the parameters of an electrical pulse suitable for stimulating a muscle or muscle group, and one or more conductor tools for delivering the electrical pulse to a muscle or muscle group, wherein the control module is configured to enable the adjustment of the parameters of the electrical pulse at levels suitable for stimulating muscles or muscle groups at a micro-level.

8 Claims, 10 Drawing Sheets

APPARATUS FOR THE DIAGNOSIS AND THERAPY OF NEURO-MUSCULAR AND OTHER TISSUE DISORDERS

This invention relates to a novel apparatus for the diagnosis and treatment of neuro-muscular injuries and disorders and anomalies in other tissues and to methods of diagnosis and treatment using the apparatus.

BACKGROUND OF THE INVENTION

The use of interferential electrotherapy treatments in physiotherapy and rehabilitation is well known. Such treatments use apparatus which electrically stimulate the neuro-muscular system via electrode pads, suction cups, laser probes, ultra-sound units and the like. Such treatments concentrate stimulus on muscle groups which have been diagnosed by conventional clinical methods to be problematic.

Often the cause of neuro-muscular malfunction or pain is difficult to diagnose since it relies heavily on interpretation of a patients perception of his problem. In cases where the symptom is a referred pain, treatment may well be focussed in an area where the pain or malfunction manifests rather than at the root cause.

Conventional diagnostic tools can identify malfunction of a muscle at a macro level but often muscle contraction can be compromised at a micro-level which is not detectable using conventional method.

SUMMARY OF THE INVENTION

In a first aspect, the present invention provides an apparatus for the diagnosis and/or therapy of neuro-muscular disorders, comprising;
- a control module for controlling the parameters of an electrical pulse suitable for stimulating a muscle or muscle group, and
- one or more conductor tools for delivering the electrical pulse to a muscle or muscle group, wherein the control module is configured to enable the adjustment of the parameters of the electrical pulse at levels suitable for stimulating muscles or muscle groups at a micro-level.

Preferably, the controlled parameters include the pulse width of the electrical pulse at levels in the range $1/30\,000$ (33 $\mu$s) to $1/7500$ (132 $\mu$s). More preferably this range includes $1/15\,000$ (66 $\mu$s).

The controlled parameters may also include pulse repetition frequency at levels which are preferably below about 500 Hz (500 IMP/s), and more preferably in the range between 1 Hz and 115 Hz (1–115 IMP/s).

The conductor tools may include any form of electrically conductive biomedical device. One such tool is the electrode pad which may optionally be used in conjunction with a conductive gel. Another suitable tool is described hereinafter as an aspect of the invention. Optionally the apparatus may comprise a selection of tools for different applications. One selection of tools may include two electrode pads of around 60 mm by 45 mm in size and four electrode pads of around 20 mm by 20 mm in size.

The controller may be analogue or digital in operation and is conveniently provided with user operable knobs or buttons to facilitate the adjustment of the controlled parameters. Such user operable devices may also be provided to enable adjustment of the polarity of the electrical pulse, to enable programming of a specified sequence of pulses between a plurality of conductor tools and/or to preset a time limit for continued stimulus over a selected muscle or muscle group.

Such devices may also be provided to enable adjustment of the intensity of the pulse and/or balance between the contracting effect of two or more conductor tools. Preferably, the control module is provided with a visual display configured to provide an image of the electrical pulse and/or confirmation of the values of the parameters adjusted.

The inventor has found that by providing electrical pulses having the parameters hereinabove described, the apparatus is capable of stimulating and detecting muscle recruitment at a micro-level, thereby enabling more accurate diagnosis and more focussed treatment of neuro-muscular disorders. It has been established that, when a muscle contracts, at a macro level, it can be compromised at a micro-recruitment level which is not detectable using conventional diagnostic methods. Normally, the muscle receptors detect the contraction of the muscle and stimulate recruitment of other muscles in the group progressively. When a nerve is stimulated, if there has been an injury, pathology or a trauma, the recruitment pattern is often compromised. Generally, when full muscle recruitment is incurred, this presents itself in the patient as a cramp, followed by tension and pain. The presence or absence of these sensations can be used to evaluate the recruitment pattern for the tested muscle group. Hence, by providing the ability to stimulate muscle groups at a micro-level, the apparatus of the present invention enables the Clinician to diagnose where a recruitment anomalie pattern exists. Once the anomalie is diagnosed, the apparatus can be used as a therapeutic tool to rehabilitate and re-educate the patient's recruitment pattern.

Typically, a patient might describe their symptoms in terms of a muscle feeling "a bit weak". Traditionally, the clinician assesses muscular weakness and lack of strength using a grading system of 1 to 5 for strength and movement—or in a more advanced method by isokinetic evaluation. Using conventional diagnostic methods, it has been difficult for Clinicians to evaluate whether the problem was lack of strength—or some other finite neuro-muscular problem, eg, whether there was a pain inhibition pattern or a malfunctioning muscle. The apparatus of the invention provides the clinician with a more detailed analysis of the recruitment behaviour of a muscle group enabling him to distinguish various forms of neuro-muscular anomalie.

The apparatus is conveniently provided in the form of a non-invasive instrument by means of which a current is passed through the body to stimulate a selected nerve that, in turn, stimulates the muscle inducing contraction. The therapeutic function of the apparatus is based on innovation of the nerve to make the muscle perform better as it contracts. The various therapeutic modalities offered by the apparatus, provide the Clinician with methods of treatment that are beneficial to improving neuro-muscular function, increasing circulation and augmenting the capillirisation of adhered areas, facilitating muscular recruitment patterns, reduction of scar tissue and adhesions, decreasing hypertonic muscular patterns at superficial and deep levels, decreasing pain patterns and acting as a post-operative therapy system for those restricted by surgery. It can be used to reduce spasm by working one muscle hard and simulating a responsive reflex so that muscle spasm can be eradicated at a deep level.

The apparatus may also be useful as an assessment tool for occupational therapy, for example, in assessing the recruitment patterns of primary and secondary muscles involved with multi-functional repetitive tasks that have a high predilection for injury.

Tests of the apparatus have shown it to be significantly more effective than other conventional electrotherapy instrument or combination of instruments available.

One useful application of the invention is in cases of inflammation or adhesion around the sciatic nerve through the gluteal region. Previously used manual treatments have merely traumatised the gluteal muscles. Another application is treatments to decrease spasm in the deep hip rotators. The apparatus can be simply set to where an over recruitment of the muscle will result in an increased expansion of the associated tissues. By working the muscles in that area they expand and stretch the scar tissue and relieve the adhesion around that muscular area. This is a segmental contraction of the muscles to increase blood to the area because, if there is scarring or adhesion, the capillaries will not form in the adhesion area. It is postulated that the use of the apparatus in this manner will improve capillarisation and blood flow assisting the body in healing itself.

A concomitant response to therapy is that the dysfunctional muscle will be in a hypertonic state and unable to recruit functionally. After effective therapy with the apparatus of the invention, the phasic contraction and relaxation of the treated muscle augments circulatory function by acting as a facilitator of blood flow through the pumping action of the muscle and associated with muscle tone.

Research using a Laser Doppler perfusion imaging system has shown impressive levels of increased circulation following therapeutic treatment with the apparatus particularly at a deeper level.

Another application is within sports medicine—in particular the rehabilitation of patients suffering from injuries caused by high-performance sports such as football and athletics.

From initial training, the high performance athlete builds muscle strength and reaches optimum performance by improving the neurological system. When the nerve/muscular relationship is impaired through injury, the muscle must be re-educated and this may require one or a combination of treatments.

The inventive apparatus can be used to diagnose the cause of the problem and in treatment to stimulate the neurological system in the affected area. If a patient has had impairment in the nerve/muscular relationship, the apparatus may be used in therapy quickly to re-educate the muscle group to work correctly.

Another major benefit from using the apparatus is in post-spinal therapy. Often, a patient who has undergone spinal surgery is very reluctant to use their muscles— especially when the surgeon has had to penetrate through four or six inches of tissue to remove a disc. The consultant may be concerned that activating muscles could induce compressive forces through the joint, or surgically addressed structure. However with the apparatus of the invention, blood flow can be stimulated to facilitate the healing process without forcing the muscles to contract in a gross manner.

The most effective use of the apparatus is in treating or diagnosing a problem frequently found in patients with spinal problems where deep-seated spasm is experienced. Unless this spasming can be eliminated, and joint manipulation attempted, the spasm will simply try to pull the joint back to its original location.

Conventional soft tissue therapy is limited to a certain depth before reaching deeper, traumatised tissues. With a spinal problem, where the muscles may be four or more inches below skin level, conventional massage cannot be used to treat it manually. However, with the apparatus of the invention, controlled penetration can release deep-seated muscular spasm. The system's ability to penetrate to depths, outside the spectrum of conventional manual therapy palpation, is one of the major benefits offered by the invention. The apparatus enables a Clinician to release deep spinal muscle spasm that influences the segments of the joints and causes compressive forces around it.

An inherent problem with surgical intervention of the spine is that many operations fail not because the surgery is inappropriate but because of the scar tissue that forms during the immediate post-operational bed rest period, resulting from the deep tissue having been cut through. By using the apparatus of the invention as a preventive means, from day one blood flow will be encouraged to flush the toxins thereby preventing the adhesions from forming.

Whilst the apparatus of the invention is particularly useful in the treatment of neuro-muscular disorders, it has various other medical and cosmetic applications. As well as the basic treatment methods mentioned above, the apparatus may be used in a number of "wet" applications where the subject undergoing diagnosis or treatment is wholly or partially immersed in a salt bath. The temperature of the bath should preferably be maintained at between about 36° C. and 42° C. In these applications, the apparatus is configured as a tripole electrode system typically having two small "active" electrodes and a larger "passive" electrode. The electrodes each comprise a highly electrically conductive particle gel mixture including silicone gel. When the subject and electrodes are immersed in the bath, current flows between one of the two active electrodes and the passive electrode. The passive electrode is immersed in the ionically conducting salt solution of the bath and the electrically relevant contact area for the active electrode is represented by the surface of the patient in contact with the solution. The conductivity of the tissue beneath the active electrodes is thereby increased and electrical pulses can be directed under control to organs located deep in this tissue. It has not previously been possible to obtain such penetration and control using conventional electrotherapy apparatus as the electrical currents supplied thereby were incapable of overcoming capacitive and ohmic resistances in the system without loss of their therapeutic effect.

In a second aspect the invention provides an apparatus for the manipulation of tissue comprising: a control module for controlling the parameters of an electrical pulse suitable for innervating nerves in the tissue, and one or more conductor tools for delivering the electrical pulse to the nerves, wherein the control module is configured to enable the adjustment of the width of the electrical pulse at levels in the range $1/30\,000$ (33 $\mu$s) to $1/7500$ (132 $\mu$s) and/or the pulse repetition frequency at levels below about 500 Hz (500 IMP/s)

More preferably this range of pulse width which is adjustable includes $1/15\,000$ (66 $\mu$s). Preferably the pulse repetition frequency is controllable in the range between 1 Hz and 115 Hz (1–115 IMP/s).

Cardiovascular therapy is another area which may benefit from the invention. For patients with diminished circulatory function, the immersion of affected limbs in water/saline solution when using the inventive apparatus has been found to dramatically improve individual's muscle contractions and neurological system in the affected limbs. Also, patients treated with the apparatus of the invention whilst being bathed in a bath with saline solution or dead sea salt at a constant temperature of about 37° C., have been found to exhibit reduced high blood pressure and improved heart muscle stimulation.

Other therapeutic applications of the apparatus may be categorised as direct; indirect and organ therapy.

Direct treatments involve the positioning of the active electrodes on areas of the body which have suffered trauma, inflamation or degeneration. Some examples include, but are not strictly limited to; whiplash trauma of the spinal column, vertebrae blockages, spondylitis, vertebrae fractures, neuralgia, sciatica, lumbar and arm syndromes, thoracic syndromes, epicondylitides, joint disease in the extremities and coxalgia.

Indirect treatments involve placing of the active electrodes on sites remote from the primary disease or symptom. Examples include but are not limited to; treating of the cranial thorax region to promote an analgesic and relaxation effect on the body and psyche, treatment in the perilumbal area to provide relief from diseases of the pelvis, treatment in the region of the upper thoracic vertebrae to relieve and cure headaches and tinnitus.

By targeting the appropriate organ tissues, diagnosis and therapy of ailments affecting, for example; the gall bladder, liver, pancreas, stomach, intestine and kidneys such as gall stones, colon spasticus, pephropathia, arterial hypertonia and arterial blood pressure abnormalities.

Other conditions which may be diagnosable or treatable using the apparatus and methods described herein include; achillodynia, adhesive capsulitis, apoplexy (peripheral), Bekhterev's disease, brachialgia, burns, carpal tunnel syndrome, cervical migraine, cervical syndrome, constipation, constusion, coxathrosis, decubital ulcer (prophylactic treatment), dislocation, distortion, Dupuytren's contracture, dysmenorrhea, edema, endangiitis, epiccondylitis, fibrositis, gonarthrosis, gout, headache, hematoma, high blood pressure, herpes zoster, intercostal neuralgia, ischialgia, joint mobilisation following surgery or cast removal, lumbago, muscle training, muscle weakness, myogelosis, occipital neuralgia, osteochondrosis, osteoporosis, prostate gland disease, Rynaud's disease, rheumatoid arthritis, scar treatment, Shceuermann's disease, sciatica, sinusitis, spondyylarthritis, spondylosis, Sudeck-Leriche syndrome, tenosynovitis, thrombus prophylaxis, trigeminal neuralgia, varicose ulcer, varicosis.

All diagnoses and treatments are made possible by the unique form of the electrical pulse provided by the apparatus of the invention which enables the innervation of nerves controlling organ function at a micro level. This innervation promotes involuntary activity in the subject muscle group or organ resulting in a variety of sensual responses in the patient, such as stabbing, pressing, pulsing and pulling. The type, location, area and intensity of the sensation as described by the patient is used in the diagnosis of abnormalities and to focus treatment in the affected areas.

In situations where employees are working in a manual environment with no particular history of specific injuries, an employer would be prudent to screen job applicants and assess the suitability of their muscles to their working environment.

The invention further provides novel conductor tools for use with the apparatus of the invention and also for use with existing electrotherapy apparatus.

A first novel conductor tool in accordance with the invention comprises:

a frame of electrically conductive material having rotatably mounted thereon an electrically conductive roller and a handle of electrically insulating material, the roller being mounted in electrically conductive communication with the frame, and means for electrically connecting the tool with a controlled electrical pulse.

Preferably the roller and handle are mounted at opposing ends of the frame. Preferably the handle is mounted at an angle substantially perpendicular to the axis of the roller. The means for electrically connecting the tool with the controlled electrical pulse are preferably provided adjacent the handle and removed from the electrically conductive roller.

Optionally the roller may be removable from the frame and replaceable with a roller of different proportions. Differently sized rollers being suitable for use with differently sized muscle groups may be provided for use with the control module.

This novel tool can be used by the Clinician to conveniently pass over a group of muscles or an organ in a smooth and continuous manner by rotation of the roller and to stimulate the muscles in the group sequentially. Patient reaction to the stimuli is monitored and can be easily rechecked by reverse rotating the roller to relocate the site of an interesting stimulus.

A second novel conductor tool in accordance with the invention is a substantially rectangular electrode pad having an active area of about 60 mm by about 45 mm. Such pads are particularly useful in the treatment of the larger muscle groups surrounding the spine.

BRIEF DESCRIPTION OF DRAWINGS

For the purposes of exemplification, some embodiments of the invention will now be further described with reference to the Figures in which.

SPECIFIC DESCRIPTION OF EMBODIMENTS

Figure 1:
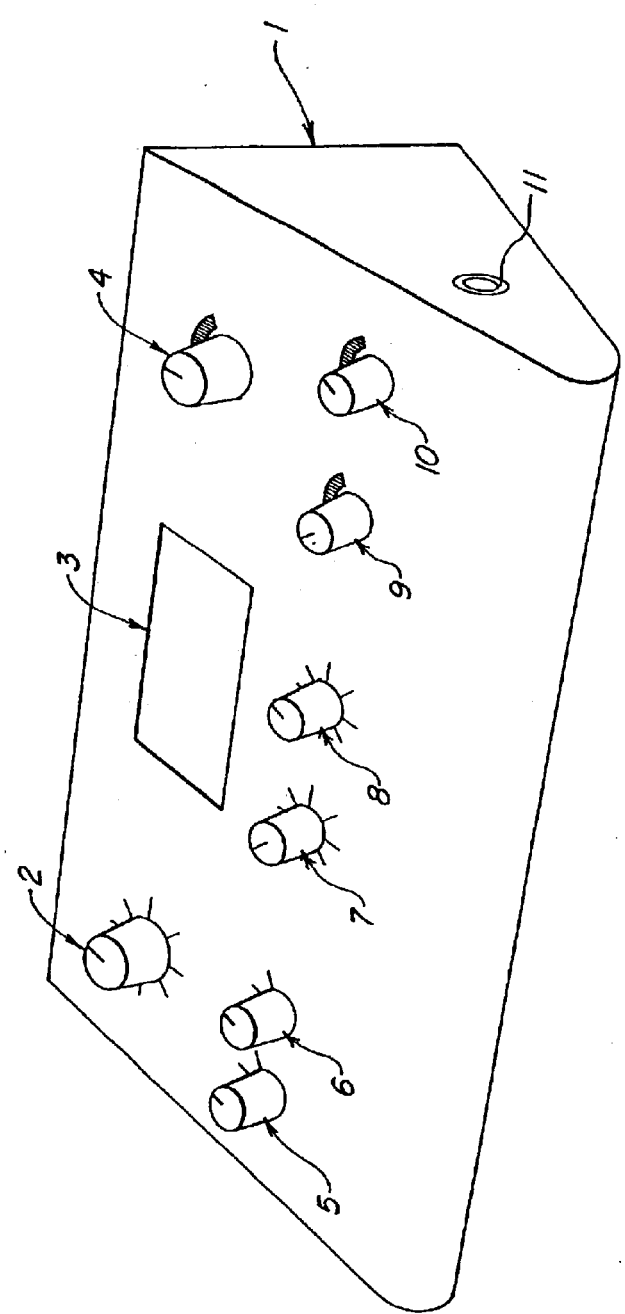
FIG. 1 illustrates a control module for use in accordance with the invention.
Figure 2:
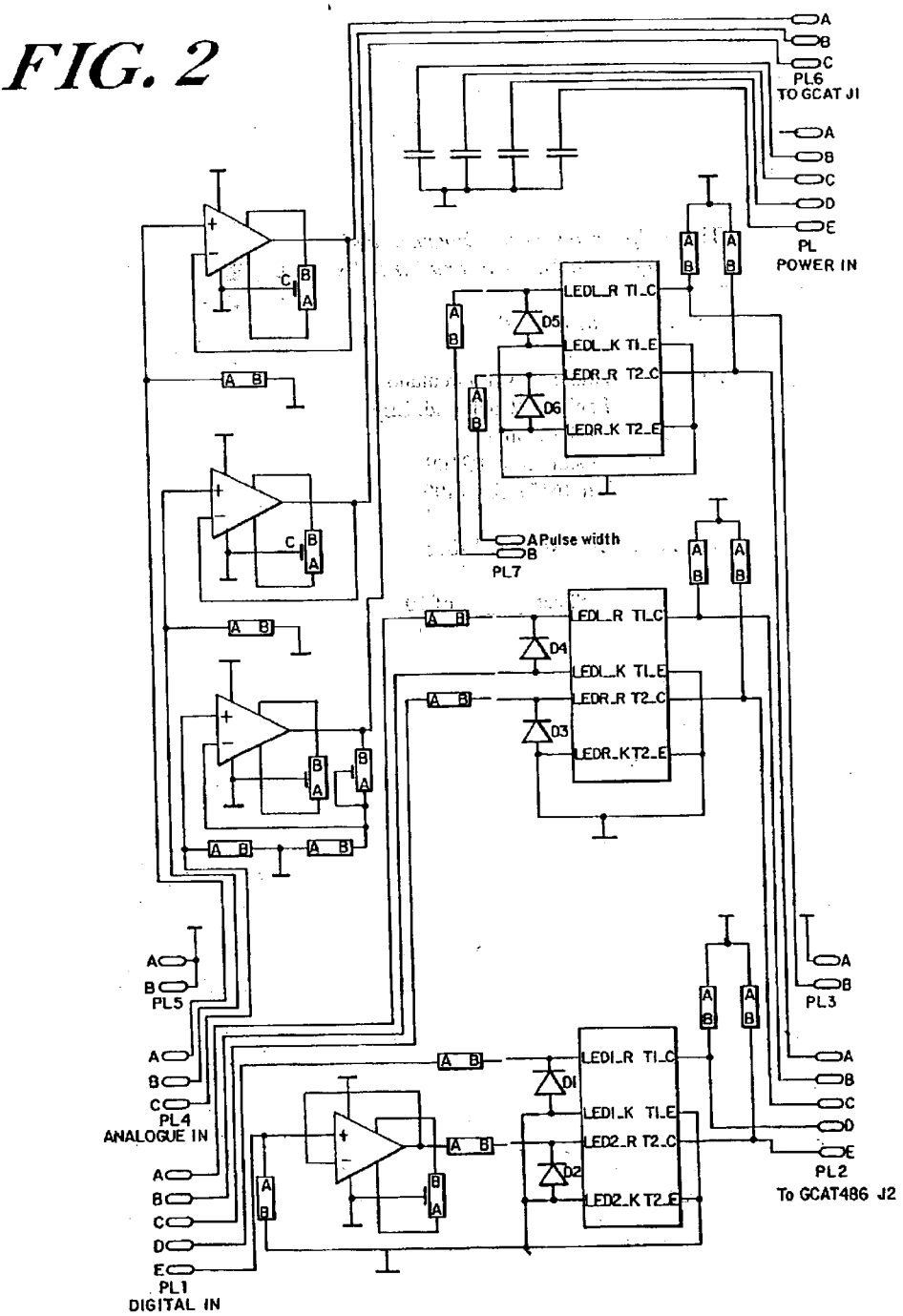
FIG. 2 illustrates one suitable PCB wiring configuration for the control module of FIG. 1.
Figure 3A:
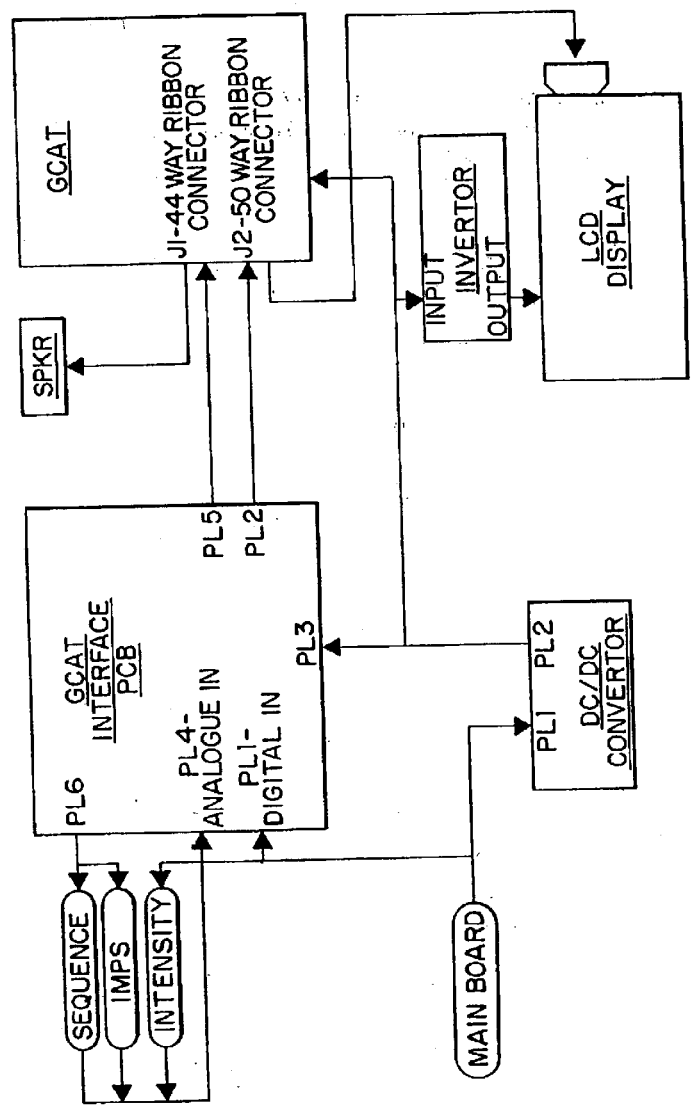
FIGS. 3(*a*) to 3(*e*) illustrate wiring diagrams for the control module of FIGS. 1 and 2.
Figure 3B:
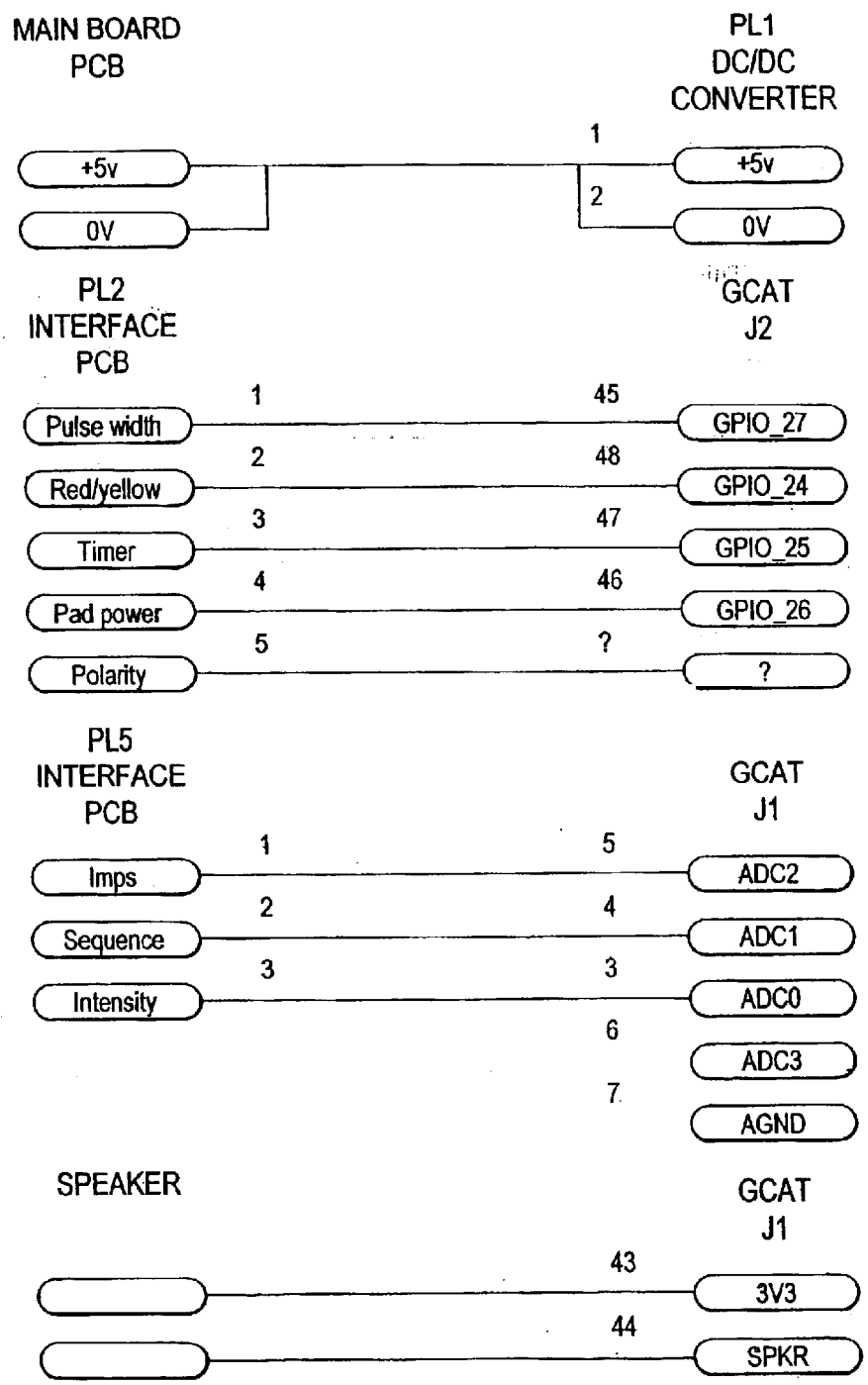
Figure 3C:
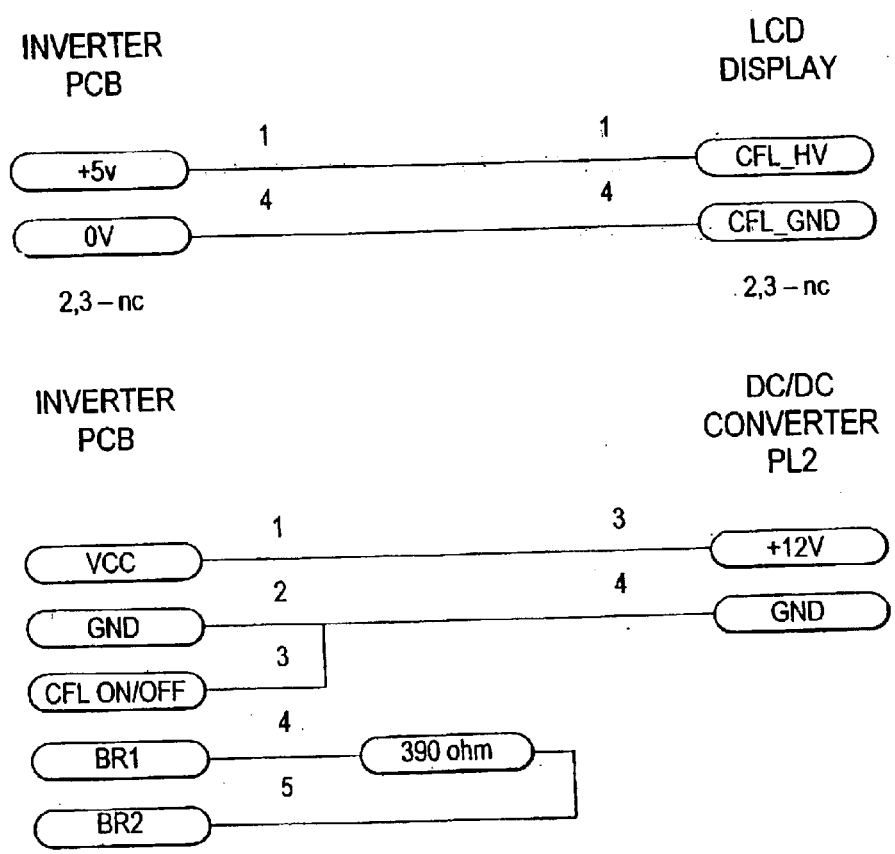
Figure 3D:
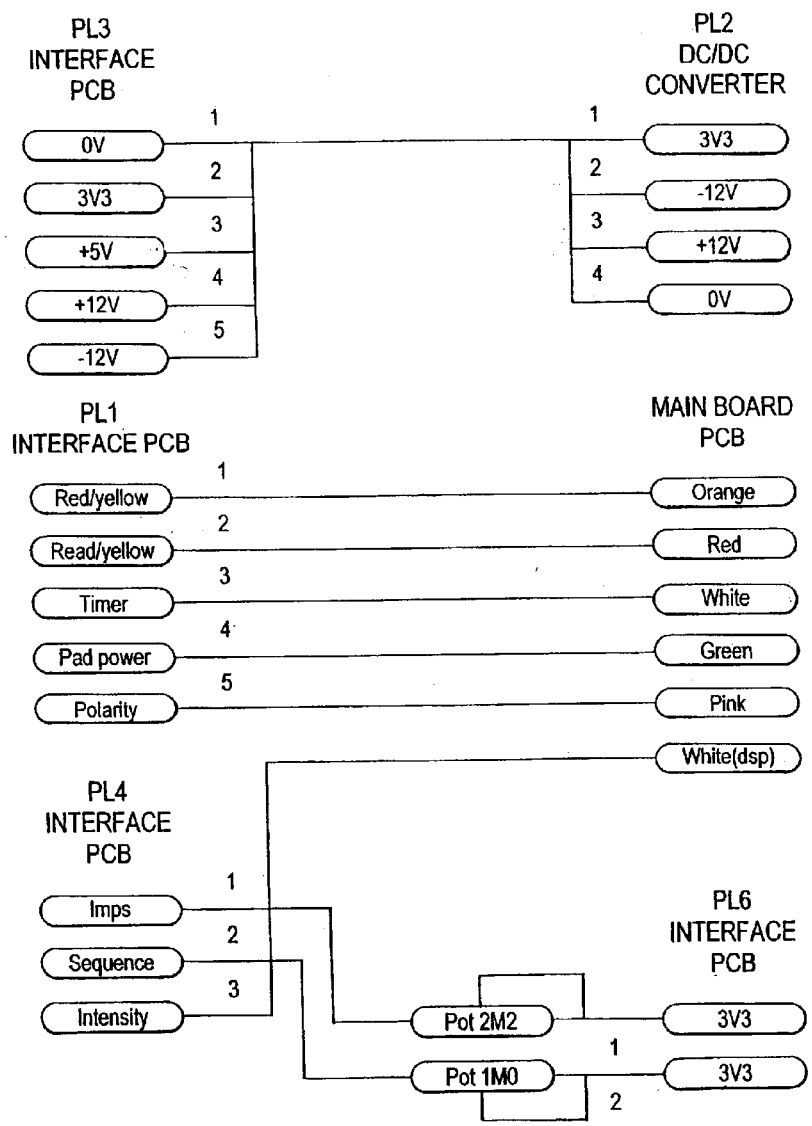
Figure 3E:
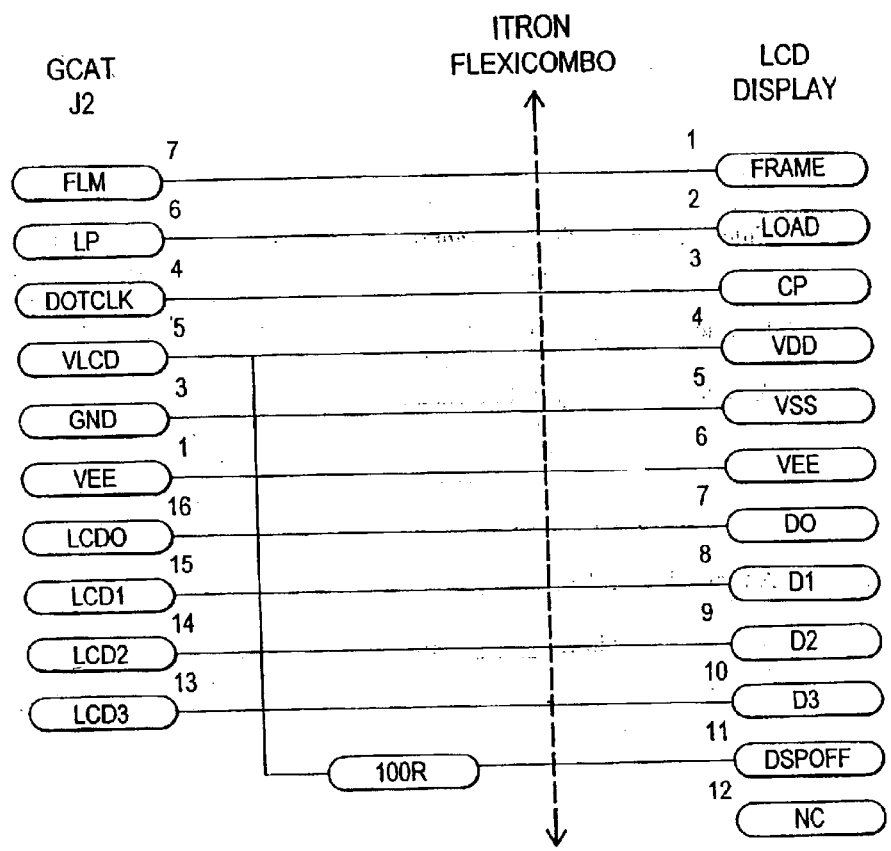
Figure 3E:
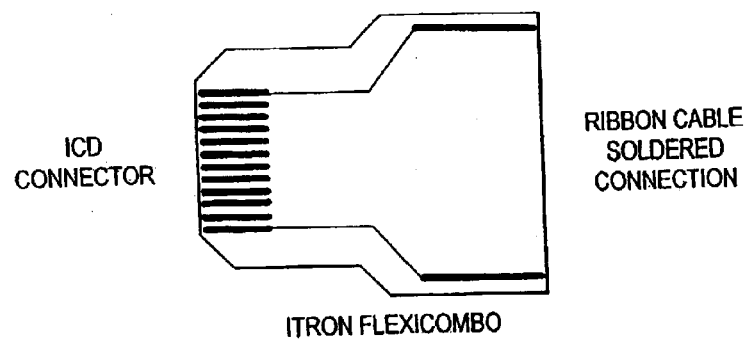

As can be seen from FIG. 1, one embodiment of the control module is presented as a box having a display screen 3 and a plurality of dials 2, 4 and 5-10. A connector loom 11 is provided for connection with a connector lead (not shown) for connecting the control module with one or more conductor tools. A power switch 1 is provided to the rear of the box which is preferably mains supplied. The dials operate respectively a time control 2, an intensity control 4, a polarity control 5, an pulse control 6, a sequence control 7, an IMP/s control 8 a balance control 9 and an active balance control 10. The control module may be used in conjunction with electrical pads or with the conductor tools illustrated in FIG. 4. The control parameters for the control module are summarised in the table below.

| Parameter | Value | Control Settings |
|---|---|---|
| Peak output voltage | 0–130 V | Intensity = min to max |
|  |  | Balance = max |
| Pulse width | 132 µs 1/7.5 K | Pulse = 1 intensity max |
| " | 66 µs 1/15 K | Pulse = 2 intensity max |
| " | 33 µs 1/30 K | Pulse = 3 intensity max |
| Pulse repetition frequency | 1 Hz–115 Hz | IMP/s = 1–115 |
| Output impedance | 1100 OHMS | Balance = max |

-continued

| Parameter | Value | Control Settings |
|---|---|---|
| Balance o/p variation | 15% | Balance = max–min |
| Output polarity | With respect to positive/negative | Polarity = + <br> Polarity = − |

In use, the conductor tools are electrically connected to the control module and are applied to the subject in the area of muscle to be tested or treated. A suitable pulse pattern is selected by adjustment of the polarity, pulse width, sequence and frequency controls. The intensity is slowly increased and the subject begins to sense the stimulation of the of the muscle. The balance controls may then be adjusted so as to create a balanced sensation in the patient between two comparable muscles or muscle groups and highlight anomalies in one group.

Figure 4:
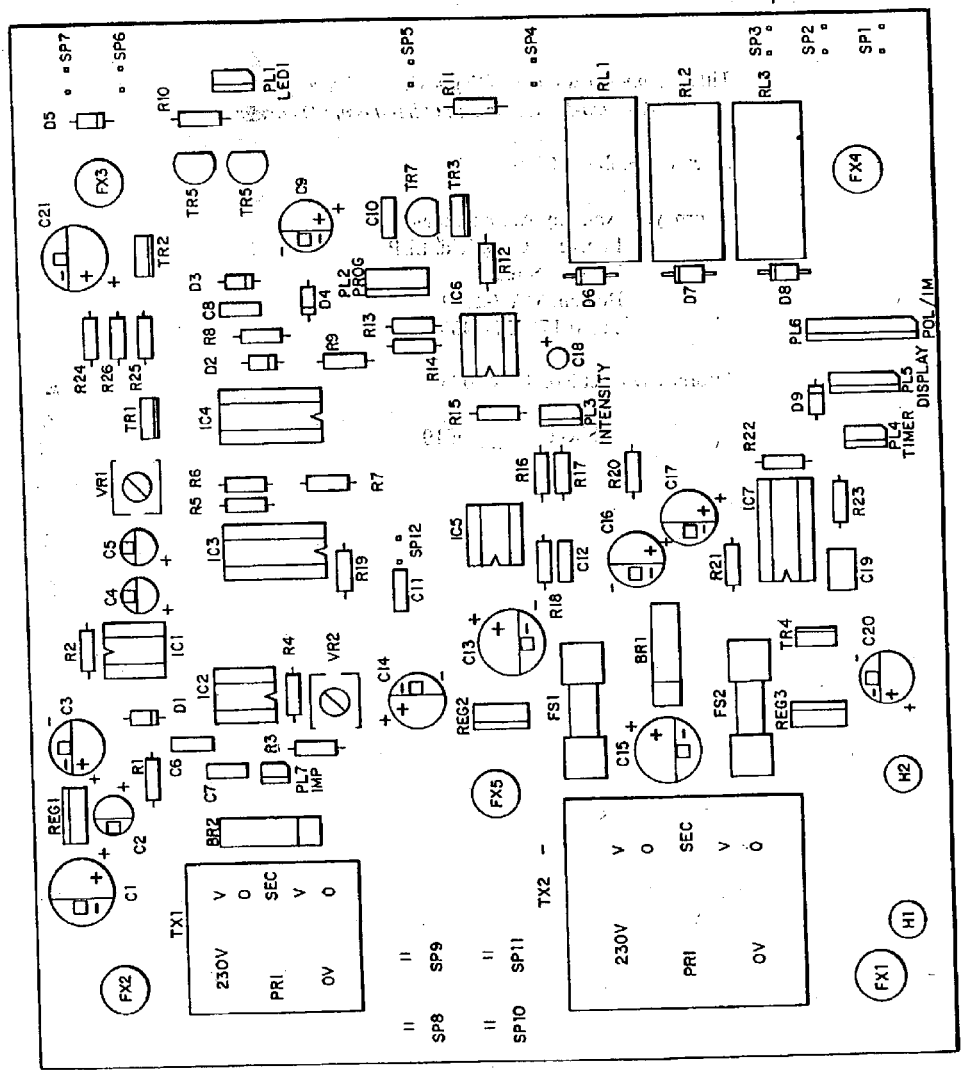
FIG. 4 illustrates a layout for the PCB board of FIGS. 1 to 3.
Figure 5:
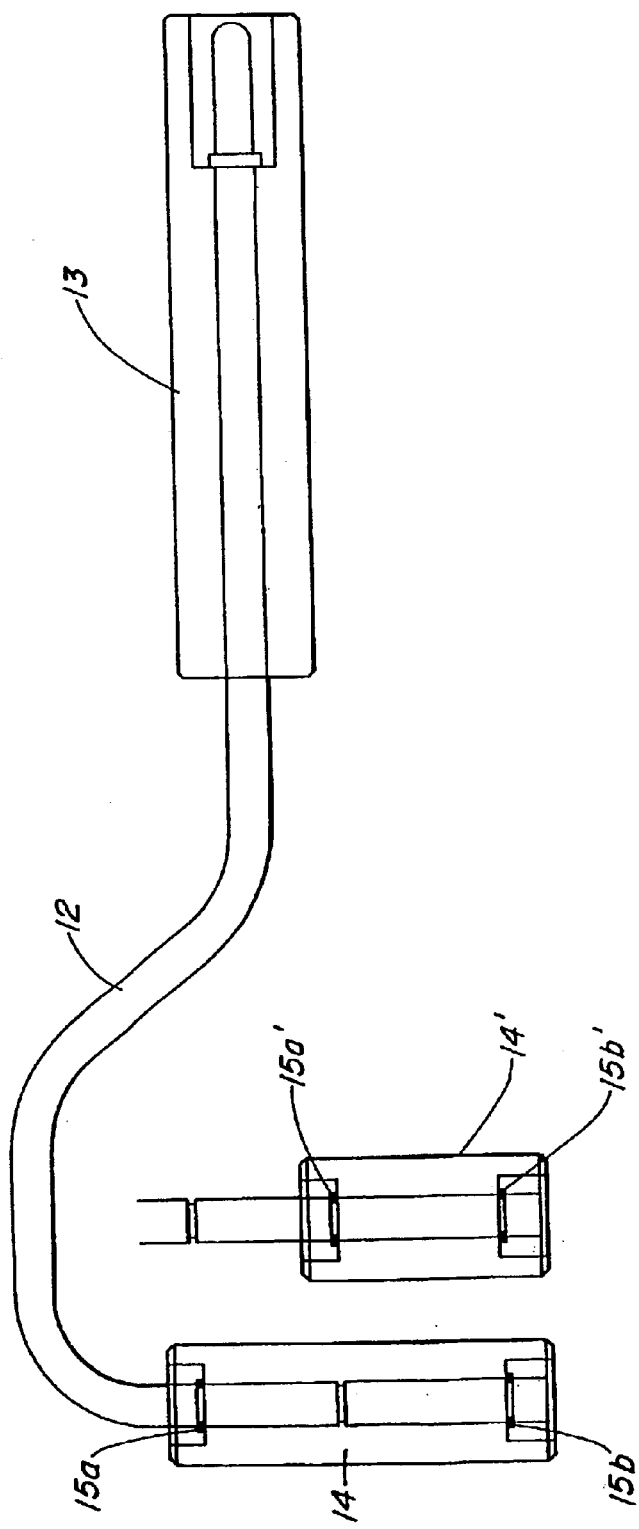
FIG. 5 illustrates one novel conductor tool in accordance with the invention.

As can be seen from FIG. 4, a conductor tool according to the invention comprises a hook-shaped metallic frame 12 having mounted at one end thereof a moulded plastic handle 13. To the hooked end of the frame is a metallic roller 14 which is rotatably mounted by means of roller bearings 15a and 15b also of an electrically conductive material such as a metal. An alternative roller 14', 15a', 15b' is also illustrated and may be interchangeable with the roller 14. A connector 16 is provided at one end of the frame, recessed in the handle for receiving a connector cable for communicating with the control module. The dimensions of the two rollers are about 60 mm length by about 18 mm diameter and about 34 mm by about 18 mm diameter.

In use, the circumference of the roller is positioned on the skin of the subject to be treated and is smoothly rolled across the area of interest stimulating nerves as it passes over them.

Figure 6:
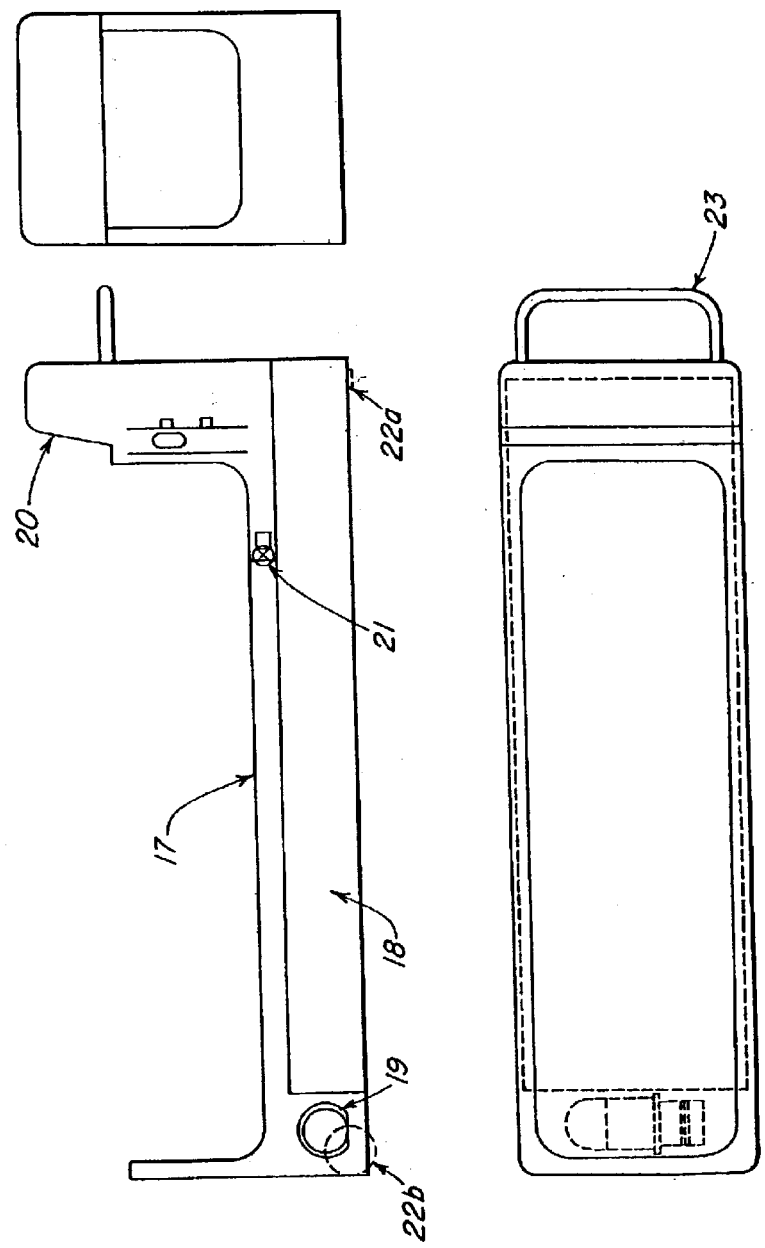
FIG. 6 illustrates a salt bathing apparatus for use in wet applications of the apparatus of FIGS. 1 to 4.

The bath of FIG. 6 comprises a basin portion 17 of approximate dimensions; 2100 mm long by 600 mm wide by 400 mm deep. Below the basin is a tank 18 for containing up to about 500 litres of saline solution. A pump 19 is located at one end of the basin for transferring solution between the tank 18 and basin 17. A control panel is mounted on a second end of the basin to facilitate operation of the pump 19 and temperature control system (not shown). The bath is mounted on rubber feet 22a at one end and rubber rollers 22b at the other to prevent slipping of the bath when patients are entering and leaving and to facilitate relocation of the bath when the feet 22a are lifted from the floor allowing the bath to be wheeled on the rollers 22b. A tubular handle 23 further facilitates relocation of the bath.

The system also has software capabilities for EMG-BIOFEEDBACK that assists the clinicians for diagnostics, patient progress reports, and ongoing evaluation.

What is claimed is:

1. An apparatus for the manipulation of tissue comprising:

a control module for controlling the parameters of an electrical pulse suitable for innervating nerves in the tissue, and one or more conductor tools for delivering the electrical pulse to the nerves, wherein the control module is configured to enable the adjustment of the width of the electrical pulse at levels in the range $1/30\,000$ ($33\,\mu s$) to $1/7500$ ($132\,\mu s$) and the pulse repetition frequency at levels below about 500 Hz (500IMP/s) and the peak output voltage of the pulse in the range 0 to 130V at least one conductor tool comprising; a frame of electrically conductive material having rotatably mounted thereon an electrically conductive roller and a handle of electrically insulting material, the roller being mounted in electrically conductive communication with the frame, and means for electrically connecting the tool with a controlled electrical pulse.

2. An apparatus as claimed in claim 1 wherein the range of pulse width levels includes $1/15\,000$ ($66\,\mu s$).

3. An apparatus as claimed in claim 2 wherein the pulse repetition frequency is controllable in a range between 1 Hz and 115 Hz.

4. An apparatus as claimed in claim 1 wherein the controlled parameters include the polarity of the electrical pulse.

5. An apparatus as claimed in claim 1 wherein the conductor tools include electrode pads.

6. An apparatus as claimed in claim 5 wherein the conductor tools include electrode pads having an active area of about 60 mm by about 45 mm.

7. An apparatus as claimed in claim 1 further comprising a bath suitable for receiving and holding saline solution at a temperature of between about 36° C. and 42° C.

8. An apparatus as claimed in claim 7 wherein the bath comprises a control panel for monitoring and/or controlling inter alia the temperature of fluid contained therein.

\* \* \* \* \*